US012745940B2

(12) United States Patent
Schouenborg et al.

(10) Patent No.: US 12,745,940 B2
(45) Date of Patent: Sep. 29, 2026

(54) MEDICAL PROTO MICROELECTRODE, METHOD FOR ITS MANUFACTURE, AND USE THEREOF

(71) Applicant: NEURONANO AB, Karlshamn (SE)

(72) Inventors: Jens Schouenborg, Lund (SE); Johan Agorelius, Malmö (SE)

(73) Assignee: NEURONANO AB (SE)

(*) Notice: Subject to any disclaimer, the term of this patent is extended or adjusted under 35 U.S.C. 154(b) by 1115 days.

(21) Appl. No.: 17/775,601

(22) PCT Filed: Nov. 13, 2020

(86) PCT No.: PCT/SE2020/000028
§ 371 (c)(1),
(2) Date: May 10, 2022

(87) PCT Pub. No.: WO2021/096403
PCT Pub. Date: May 20, 2021

(65) Prior Publication Data

US 2022/0401001 A1 Dec. 22, 2022

(30) Foreign Application Priority Data

Nov. 13, 2019 (SE) .................................. 1900195-7

(51) Int. Cl.
*A61B 5/268* (2021.01)
*A61B 5/1473* (2006.01)
(Continued)

(52) U.S. Cl.
CPC .......... *A61B 5/268* (2021.01); *A61B 5/14735* (2013.01); *A61B 5/273* (2021.01);
(Continued)

(58) Field of Classification Search
CPC ......... A61B 5/262; A61B 5/268; A61B 5/273; A61B 5/293; A61B 5/294; A61B 5/14735;
(Continued)

(56) References Cited

U.S. PATENT DOCUMENTS

2003/0028224 A1 2/2003 McVenes et al. ............... 607/36
2010/0010550 A1 1/2010 Ponomarev et al. ............. 607/3
(Continued)

FOREIGN PATENT DOCUMENTS

WO WO 2005/011806 A1 2/2005
WO WO 2007/040442 A1 4/2007
(Continued)

OTHER PUBLICATIONS

International Search Report mailed Jan. 18, 2021 in corresponding PCT International Application No. PCT/SE2020/000028.
(Continued)

*Primary Examiner* — Livius R. Cazan
(74) *Attorney, Agent, or Firm* — OSTROLENK FABER LLP

(57) ABSTRACT

A proto-microelectrode, a proto-microelectrode bundle and array, a method of manufacture of the proto-microelectrode, and a method of using the proto-microelectrode, the proto-microelectrode being capable of forming a microelectrode upon implantation into soft tissue, and includes an oblong electrode body; an optional first coat of electrically non-conducting material on the electrode body; a second coat of water insoluble flexible polymer material enclosing, at a distance, the electrode body and the first coat, the second coat including one or more through openings; a first layer of ice disposed between the electrode body and the second coat.

23 Claims, 8 Drawing Sheets

(51) Int. Cl.
*A61B 5/273* (2021.01)
*A61B 5/294* (2021.01)

(52) U.S. Cl.
CPC ...... *A61B 5/294* (2021.01); *A61B 2562/0209* (2013.01); *A61B 2562/028* (2013.01); *A61B 2562/04* (2013.01); *A61B 2562/125* (2013.01); *A61B 2562/164* (2013.01)

(58) Field of Classification Search
CPC ...... A61B 2562/0209; A61B 2562/028; A61B 2562/125; A61N 1/05
See application file for complete search history.

(56) References Cited

U.S. PATENT DOCUMENTS

| | | | | |
|---|---|---|---|---|
| 2010/0145216 | A1* | 6/2010 | He | A61B 5/388 600/544 |
| 2013/0320273 | A1 | 12/2013 | Kotov et al. | 252/511 |
| 2020/0093512 | A1* | 3/2020 | Schouenborg | A61N 1/0531 |

FOREIGN PATENT DOCUMENTS

| | | | |
|---|---|---|---|
| WO | WO 2013/191612 | A1 | 12/2013 |
| WO | WO 2017/095288 | A1 | 6/2017 |
| WO | WO 2018/217147 | A1 | 11/2018 |
| WO | WO 2010/144016 | A1 | 12/2020 |

OTHER PUBLICATIONS

Written Opinion mailed Jan. 18, 2021 in corresponding PCT International Application No. PCT/SE2020/000028.

* cited by examiner

A,C
A
C
B
R
3,8
1b
1a
1
2
3
4
4a
4b
5
6
7
8
9
9'
9''
11
11'
25
H

MEDICAL PROTO MICROELECTRODE, METHOD FOR ITS MANUFACTURE, AND USE THEREOF

CROSS-REFERENCE TO RELATED APPLICATIONS

The present application is a 35 U.S.C. §§ 371 national stage application of PCT/SE2020/000028, filed Nov. 13, 2020, which claims priority to Swedish Application No. 1900195-7 filed Nov. 13, 2019, the contents of which are incorporated herein by reference. The PCT application was published in English.

FIELD OF THE INVENTION

The present invention relates to a medical proto microelectrode for full or partial disposition in soft tissue, to a microelectrode so disposed, to a method of producing the proto microelectrode, and to its use. Furthermore, the present invention relates to bundles and arrays comprising two or more proto electrodes of the invention and to corresponding micro electrode bundles and arrays disposed fully or partially in soft tissue.

BACKGROUND OF THE INVENTION

An important feature of a microelectrode for insertion into soft mammalian tissue (e.g. nervous tissue) is ability to flexibly follow tissue movements once implanted. For such flexible microelectrodes there is, however, a need for structural support during insertion into the tissue. A measure to increase the structural integrity of a flexible microelectrode has been to apply a layer of degradable or dissolvable material which in dry state provides sufficient total integrity of the microelectrode for successful insertion into soft tissue. While biocompatible materials facilitating the insertion of a microelectrode are known by the art, the change of (physical) state once inserted transitionally influences the composition of the tissue fluid in the vicinity of the measurement volume. The transitional change of the tissue fluid in the measurement area is compounded if the degradable/dissolvable material is wrapped in an insoluble envelope having only one opening or a few openings. Since tissue fluid needed for the change of state of the insertion facilitating material communicates only through the opening(s) which also defines the location of electrical interaction between soft tissue and electrically conductive element. Additionally, during the change of state of the insertion facilitating material dissolved compounds will diffuse through the opening into the tissue to be monitored (or stimulated) until equilibria between internal solutions and external tissue fluids are formed. The above presented dynamics often perturb the physiological state of the tissue to be recorded or stimulated specifically at a time frame immediately after positioning of the microelectrode within the soft tissue. This is problematic when rapid assessment of tissue function is needed, for example in a clinical diagnostic situation.

A useful microelectrode known in the art (WO 2013/191612) comprises or substantially consists of a flexible oblong, electrically conducting electrode body having a front (distal) end and a rear (proximal) end, the electrode body comprising or consisting of a metal or a metal alloy or an electrically conducting form of carbon or an electrically conducting polymer or a combination thereof, a (second) coat of electrically insulating, water insoluble and flexible, preferably also resiliently flexible, polymer material surrounding the electrode body over its entire length or at least over a portion extending from its front end towards its rear end and disposed at a distance from the electrode body so as to define a tubular interstice filled with aqueous body fluid and/or with a gel comprising aqueous body fluid.

The proto microelectrode from which the microelectrode of WO 2013/191612 is formed in situ upon insertion of the proto microelectrode into soft tissue comprises or substantially consists of a flexible oblong electrode body of electrically conducting material having a front (distal) end and a rear (proximal) end, the electrode body comprising or consisting of a metal or a metal alloy or an electrically conducting form of carbon or an electrically conducting polymer or a combination thereof, a first coat of a water soluble and/or swellable and/or degradable material on the electrode extending along the electrode body at least over a portion extending from its front end towards its rear end, and a second coat of electrically insulating, water insoluble flexible polymer material on the first coat, the second coat comprising one or more through openings at or near the front end. Upon insertion of the proto electrode of WO 2013/191612 into soft tissue the electrode of the invention is formed by the action of aqueous body fluid on the first coat, which is dissolved and/or degraded and/or swollen. Access of aqueous body fluid to the first coat is provided by said through openings in the second coat. The material of the first coat can be one which is readily soluble in aqueous body fluid, such as glucose, or one which is not readily soluble in aqueous body fluid, such as glucose acetate, or one of intermediate solubility, such as partially acetylated glucose. A material of the first coat of a desired dissolution rate can also be obtained by combining materials of different solubility and/or dissolution properties, such as a combination of a low molecular carbohydrate and a peptide or protein, for instance the combination of glucose and gelatin.

While the first coat provides physical stability to the proto-electrode of WO 2013/191612 its transformation in situ to a corresponding microelectrode is time-consuming due to the need of having it solubilized by aqueous body fluid and to the need of adjacent soft tissue resorbing the solubilized matter to establish natural physiological conditions. In addition, the material to be resorbed puts a physiological load on that tissue and may cause stress on it and changes in the tissue. Uptake of water may for example cause local dehydration of extracellular space and of cells in the vicinity of the through openings. Moreover, the materials to be resorbed will diffuse out in the vicinity of the through openings creating a relatively high local concentration in the tissue just outside the through opening. This is problematic since cells resident in the tissue changed in this manner will be the same cells from which electrical signals or electrochemical signals are recorded by the electrode or which may be electrically stimulated by it.

Especially important is the spatial volume of soft tissue situated up to about 50 μm from the opening in any direction. During and after the change of state of the insertion facilitating material (e.g. gel-forming material) there is a significant difference as to the composition of the tissue fluid and the solution inside the envelope of water insoluble flexible polymer material. After some time an equilibrium regarding multiple parameters of the tissue fluid and the solution inside the envelope will be obtained. The equilibrium of the tissue fluid and the internal solution can only be provided by fluid streams across the opening of the water insoluble flexible polymer material. This motion of solution across the opening (specifically the diffusion of internal solution into surrounding soft tissue) will significantly influence the metabolic load of the soft tissue volume situated up to about 50 μm from the opening and thereby altering homeostasis and thereby potentially influence signal pattern observed by the electrically conductive element.

WO 2018/217147 relates to microelectrodes reducing tissue damage, specifically while introduced into soft tissue. An important feature of the microelectrode is the temperature of the microelectrode when introduced into soft tissue. More specifically, the distal terminal section of the microelectrode features a temperature substantially below body temperature, such as in the region of from 7° C. to 3° C. or even below zero degrees. The distal terminal section is covered with a layer of a material capable of forming a gel in contact with aqueous body fluids. According to an embodiment the layer of gel forming agent can be provided with a coat of ice. The optional layer of ice on the gel forming agent may be the outermost layer of the microelectrode of WO 2018/217147. The presence of a layer of gel forming material surrounding the electrode body provides the microelectrode with sufficient rigidity to be successfully introduced into soft tissue.

OBJECTS OF THE INVENTION

An important object with the invention is the provision of a proto-microelectrode which improves the functionality of flexible microelectrodes and specifically the improvement of the functionality of the microelectrode within a time period immediately after positioning of the microelectrode.

A further object of the invention is the provision of a proto-microelectrode reducing or even mitigating the perturbation of homeostasis of soft tissue, specifically tissue localized in the vicinity of the part of the electrically conductive element being in electrical contact with the surrounding solution/fluid.

A still further object is the provision of a proto-microelectrode reducing or mitigating the metabolic load of the soft tissue, specifically tissue localized in the vicinity to the part of the electrically conductive element being in electrical contact with the surrounding solution/fluid.

Yet another object of the invention is to provide a method of forming in situ in soft tissue a microelectrode of the kind disclosed in WO 2013/191612 by insertion of a proto-microelectrode into the tissue, the proto-microelectrode being devoid of the drawback of the known proto-microelectrode by being capable of rapid transformation to a corresponding microelectrode and not comprising soluble material capable of affecting adjacent tissue upon dissolution such as by water uptake causing local dehydration.

Another object of the invention is to provide a corresponding proto-microelectrode and a method for its production.

Further objects of the invention will become apparent from the following summary of the invention, the description of preferred embodiments thereof illustrated in a drawing, and from the appended claims.

SUMMARY OF THE INVENTION

In this application "electrode" signifies "microelectrode". Electrode body means an entity capable of conducting electric current. "Water insoluble" signifies insoluble in aqueous body fluid, that is, interstitial or extracellular fluid but also serum. "Electrode contact" signifies direct contact of electrode portions with tissue. A flexible electrode body designates an electrode body which, without supporting means, could not be successfully introduced into soft tissue. As used here, a flexible electrode body without supporting means, would not be able to be precisely positioned as the flexible electrode would be deflected by the soft tissue. "Electrically insulating" signifies electrically insulating at voltages/currents used with a device implanted in human soft tissue. "Oblong" signifies a structure of a length greater by a factor of five or more, in particular of ten or more, than its diameter. "Swellable" means an expansion of volume by a factor of at least 1.2 at contact with aqueous body fluid. "Porous" signifies permeable for aqueous body fluids and biomolecules dissolved therein. As will be explained below in more detail "microelectrode" signifies a microelectrode of the invention in a state inserted into soft tissue and partially or fully equilibrated with body fluid in the tissue, whereas "proto microelectrode" and "proto electrode" signifies a corresponding microelectrode of the invention prior to insertion into the tissue.

According to the present invention is disclosed a proto-microelectrode of the aforementioned kind, which solves or at least reduces one or more of the problems associated with proto-microelectrodes known in the art. The microelectrode of the invention is formed upon insertion of the proto-microelectrode into soft tissue such as nervous, endocrine or muscular tissue including connective and epithelial tissue covering nervous, endocrine or muscular tissue or fluidic compartments. The proto-microelectrode of the invention reduces the risk of tissue damage during and upon insertion, such as by stress on tissue contacted by it or, in particular, by local dehydration. Another advantage of the proto-microelectrode of the invention is that, once implanted into tissue, it is substantially more rapidly, such as twice or trice or ten times as fast, transformed into a microelectrode than known proto-microelectrodes of similar kind provided with a layer of dissolvable or degradable material in which their electrode body is embedded, thereby substantially preventing local dehydration.

The present invention departs from a proto-microelectrode of generally known kind, such as the proto-microelectrode disclosed in WO 2013/191612, of which the coat of water soluble and/or swellable and/or degradable material on the partially electrically insulated electrode body is substituted by frozen water or a frozen aqueous solution, in particular a frozen physiological aqueous solution containing dissolved inorganic and/or organic compounds in a physiologically acceptable concentration. The aqueous solution has a preferred freezing point of from −5° C., more preferred of from −3° C. or −2° C., in particular from −1.5° C., preferably from −1.0° C., particularly preferred from −0.8° C. or −0.7° C., or even from −0.5° C. to 0° C.

Furthermore, in stark contrast to the microelectrode of WO 2018/217147, the coat of ice of the proto-microelectrode of the present invention is disposed between the electrode body and a second coat of water insoluble flexible polymer.

The coat of ice may provide added transient structural integrity to the proto-microelectrode for the successful insertion into soft tissue. According to the present invention is thus disclosed a proto-microelectrode capable of forming, upon insertion into soft tissue, a microelectrode, the proto-microelectrode comprising or consisting of:

- an oblong electrode body of electrically conducting material having a front (distal) end and a rear (proximal) end, the electrode body comprising or consisting of metal or metal alloy or an electrically conducting form of carbon or an electrically conducting polymer or a combination thereof;

an optional first coat of electrically non-conducting material on the electrode body extending along it from its rear end towards its front end, the electrode body comprising one or more sections not covered by the first coat;

a second coat of water insoluble flexible polymer material disposed at a distance from and enclosing the electrode body and, if present, the first coat or a portion thereof, the second coat comprising one or more through openings or windows;

a first layer of ice optionally comprising pharmacologically active agent disposed between the electrode body and the second coat.

According to an embodiment the proto-microelectrode does not comprise water soluble and/or swellable and/or degradable materials A further embodiment relates to a proto-microelectrode which does not comprise materials capable of forming gels in contact with aqueous body fluids.

A further embodiment is that the first layer of ice (frozen aqueous solution) has dimensions contributing, suitably significantly contributing, to the rigidity of the proto-microelectrode enabling a successful insertion into soft tissue.

While it is generally preferred for the electrode body to be flexible, in particular resiliently flexible, stiff electrode bodies are specifically preferred for applications that don't require flexibility.

The surface of the electrode body can be smooth but may also be provided with nano- or microstructures to increase its area, thereby reducing the impedance of the electrode body.

While the electrode is preferably of a noble metal or an alloy of noble metals or comprising noble metals such as gold, silver, platinum, iridium, other biologically acceptable metals such as stainless steel and tantalum can also be used as well as gold plated copper. Instead of metal or metal alloy the electrical conductor may consist of or comprise an electrically conducting polymer. Furthermore, the electrode may also comprise carbon such as graphite or graphene. Alternatively, the electrode may comprise a combination of noble metal or alloy of noble metals and carbon (such as graphite or graphene). The electrode body may also be chemically modified to be used in voltammetry based methods.

The diameter of the electrode is typically under 100 μm, preferably under 50 μm and even more preferably under 10 μm.

The first layer of ice optionally comprising pharmacologically active agent has a melting point of from −5° C., more preferred of from −3° C. or −2° C., in particular from −1.5° C., preferably from −1.0° C., particularly preferred from −0.8° C. or −0.7° C., or even from −0.5° C. to 0° C.

In a preferred embodiment of the invention the metallic electrode body is multi-stranded.

It is preferred for one or more of said one or more through openings to be disposed in distal portion(s) of the second coat. Alternatively, in particular for an application in which it is desired to receive and/or transmit electrical signals by the electrode from or to neurons disposed near the surface of a soft tissue, it is preferred for one or more of said one or more through-openings to be disposed in proximal portions (s) of the second coat. In particular, one or more of said one or more through openings, in particular all through openings, are disposed in a portion of the second coat extending from half of its length to the proximal end, in particular from two thirds or three fourths of its length to the proximal end, most preferred in a portion extending in a distal direction from the proximal end over a distance of 5 percent or 10 percent of the length of the electrode body.

A through opening has a diameter or a maximal diameter of from about 1 or 2 μ to about 60 μm, more preferred from 15 μm to 50 μm, most preferred from 25 μm to 40 μm. In the event that very small openings are used, such as openings from about 1 μm to about 15 μm in diameter, in particular of a diameter or maximal diameter of below 10 μm, it is preferred to use more than one opening, in particular more than three or five or event ten or twenty openings.

According to a preferred embodiment of the invention the second coat has a wall thickness that is smaller than the diameter of the electrode body or the diameter of the combination of electrode body comprising a first coat, in particular has a thickness of less than 50%, preferably of less than 30%, most preferred of less than 15% or 10% of said diameters. A preferred wall thickness of the second coat is up to 20 μm, in particular is from 2 μm to 5 μm.

A preferred diameter of the electrode body is from 1 μm to 100 μm or more, in particular from 2 μm to 10 μm or 25 μm or 40 μm.

According to another preferred aspect of the invention, the proto-microelectrode comprises a portion of the second coat in the form of a bellows tube.

According to another preferred aspect of the invention, the proto-microelectrode comprises an electrical lead attached to a proximal portion thereof, wherein the second coat extends to and encloses a distal portion of the lead.

According to a particularly preferred aspect of the invention, the proto-microelectrode of the invention comprises a second layer of ice optionally comprising pharmacologically active agent disposed on the second coat.

According to the present invention is furthermore disclosed a method of generating a micro-electrode disposed in soft tissue comprising inserting the proto-microelectrode of the invention into the tissue, wherein the proto-microelectrode has a temperature at the start of insertion of below 0° C., in particular of below −1° C. or −2° C., preferably of below −5° C.

The proto-microelectrode of the invention can be used for implantation into soft tissue, such as nervous and endocrine tissue.

Further, the proto-microelectrode of the invention can be used for monitoring electrochemical signals.

According to a further embodiment, the electrode body of the proto-microelectrode may be chemically modified to be used in voltammetry based methods According to the present invention is also disclosed a method of manufacture of a proto-microelectrode for insertion into soft tissue, comprising: providing a first pre-stage microelectrode comprising or consisting of an oblong electrode body of electrically conducting material having a front (distal) end and a rear (proximal) end; optionally comprising a first coat of electrically non-conducting material on the electrode body extending along it from its rear end towards its front end, the electrode body comprising one or more sections not covered by the first coat; a second coat of water insoluble flexible polymer material disposed at a distance from and enclosing the electrode body or a portion thereof, the second coat comprising one or more through openings; a layer of porous carbohydrate material disposed between the electrode body and the second coat; providing a second pre-stage microelectrode by substituting the layer of porous carbohydrate material by water optionally comprising pharmacologically active agent; cooling the thus transformed second pre-stage microelectrode to a temperature capable of transforming the layer of water optionally comprising pharmacologically active agent to a first layer of ice for a time sufficient for complete transformation.

According to a preferred aspect of the invention the layer of porous carbohydrate material is formed by providing an aqueous solution comprising or consisting of water and more than 20% by weight of glucose and/or other mono- or disaccharide of high solubility in water or a combination thereof, in particular of more than 40% or 45% by weight; providing a form comprising a channel of preferably cylindrical form closed at its one end; disposing the electrode body with its distal end foremost in the channel; filling the channel up to a desired proximal level of the electrode body with said aqueous solution; cooling the form to a freezing temperature of the aqueous solution; separating the electrode body with adhering frozen aqueous carbohydrate solution from the form and disposing it, while keeping it frozen, in an low-pressure environment for a time sufficient to transform the frozen aqueous solution to said layer of porous carbohydrate. A preferred pressure in the low-pressure environment is below 1000 Pa, in particular below 500 Pa or 200 Pa. To facilitate removal of the thus formed pre-stage microelectrode the form is made separable in a plane in which the cylinder axis or the axis of the cylindrical channel or channel of other rotationally symmetric form is disposed.

An alternative method for transforming the layer of frozen aqueous carbohydrate solution adhering to the electrode body to one of dry carbohydrate is by placing the form with its contents in an oven at a temperature above room temperature, such as at a temperature of 50° C. or more until transformation of the aqueous phase into a caramelized state followed by removal of the product from the form.

According to a preferred aspect of the method of the invention the proto-microelectrode is provided with a second layer of ice optionally comprising pharmacologically active agent disposed on the second coat.

According to another preferred aspect of the invention a first pre-stage microelectrode comprises a flexible electrical lead attached to the proximal end of the electrode body, the second coat being provided in a manner so as to enclose a distal terminal portion of the electrical lead.

The proto-microelectrode of the invention can be used for implantation into soft tissue of any kind, in particular nervous or endocrine tissue.

It is preferred for the electrode body to be flexible, in particular resiliently flexible.

The front end of the electrode body coincides or about coincides with the front end of the second coat of flexible, water insoluble polymer. The rear end of the electrode body can coincide with the rear end of the electrode or extend further in a proximal direction, such further extension, while materially integral with the electrode body, not being considered to be comprised by the electrode proper but to serve as an electrical lead connecting the electrode with an electrode control unit. Alternatively, a separate lead is provided between the rear end of the electrode body to which it is soldered or otherwise joined in an electrically conducting manner, and an electrode control unit disposed at a distance from the electrode intra-corporeally or extra-corporeally. The separate lead or the lead integral with the electrode body extending proximally from the electrode is electrically insulated. The oblong flexible electrode body corresponds to, for instance, a functionally equivalent element in a microelectrode known in the art, such as in WO 2010/144016 A1 and WO 2007/040442 A1.

If the second coat of water insoluble flexible polymer material does not extend to the rear end of the electrode body the portion thereof not covered by the second coat is electrically insulated by other means, for instance by a water insoluble lacquer.

The water insoluble flexible, preferably resilient, polymer material of the second coat has a preferred wall thickness that is substantially smaller than the diameter of the electrode body and the wall thickness of the first coat, such as by a factor of five or even ten or more. A preferred thickness of the electrode body of the proto electrode and the corresponding electrode of the invention is from 1 μm to 100 μm or more, in particular from 2 μm to 10 μm or 25 μm or 40 μm, the wall thickness of the first coat being within the range of from 100 nm to 5 μm, while a preferred thickness of the second coat is in the range of a few μm, such as from 2 μm to 5 μm but even up to 20 μm or more. However, in certain applications in which a very thin electrode body is used, the wall thickness of the second coat can be larger than the diameter of the electrode body, such as by a factor of 2 or 10 or more.

The second coat must be biocompatible and sufficiently flexible to allow it to flex with a flexible electrode body, in particular without restraining flections of the electrode body. The second coat is preferably resiliently flexible. A particularly preferred insulating polymer material of the second coat is a Parylene, such as Parylene C. Other preferred insulating materials comprise polytetrafluoroethylene, polyurethane, polyimide, various kinds of silicones and synthetic or natural rubber. The insulating polymer coat has a minimum thickness that provides sufficient electrical insulation. For Parylene C a minimum thickness of 2-5 μm is adequate in many applications. In congruence with the first coat, the second coat is preferably rotationally symmetric around a central axis shared with the first coat, that is, the second coat is preferably cylindrical or at least a portion intermediate between its front and rear portions is cylindrical.

According to a still further aspect of the invention the provision of a second coat comprising bellows shaped portions provides improved anchoring capability for the electrode of the invention in comparison with that of an electrode with a cylindrical second coat. The one or more pharmacologically active agents of the first layer of ice are water soluble or water dispersible and comprise or consist of agents influencing the function of neurons like GABA, glycin, dopamine, serotonin, neuroleptics, sedatives, analgesics, agents exerting a trophic effect on nerve cells, for instance NGF, and gene vectors for long term effect. Other useful pharmacologically active agents include anti-inflammatory agents, anticoagulants, β-receptor blockers, antibodies and nutrients. In principle, any pharmacologically active agent of interest can be used and is within the scope of the present invention, provided that it is sufficiently soluble in aqueous body fluid.

According to another preferred aspect two electrodes of the invention are used in combination to provide bipolar stimulation. For this purpose, two proto electrodes of the invention disposed in parallel and abutting each other are joined at the exterior face of their second coats by gluing or by enclosing them in a third flexible polymer coat, for instance of Parylene C. The glue may be of same material as the second coat, such as of a parylene, or of a different material but may also be of a material that is dissolvable or degradable in aqueous body fluid such as gelatin.

It is also within the ambit of the invention to provide bundles and arrays comprising two or more proto-microelectrodes of the invention, such as three or four microelectrodes of the invention, and to use them for implantation. An array of the invention comprises two or more microelectrodes of the invention disposed at a distance from each other joined at their proximal portions by an array base which can be of degradable or non-degradable materials. A bundle of two or more proto-microelectrodes comprises a bundling element enclosing them at a their proximal portions. The bundling element can be of degradable or non-degradable materials The pre-stage of the proto-microelectrode thus produced is further transformed by placing it in container containing an aqueous solution, for instance one comprising electrolyte(s) such as $Na^+$, $K^+$, $Ca^{2+}$, $Mg^{2+}$, $Cl^-$, $HCO_3^-$, $HPO_4^{2-}$, nutrients such as glucose and other monosaccharides, amino acids, vitamins, and the like, to exchange the aqueous phase formed inside of the flexible, water-insoluble layer by diffusion trough the one or more holes or windows in the second coat. The aqueous solution may comprises any combination of ammonium, calcium, iron, magnesium, potassium, quaternary ammonium, sodium, copper, acetate, carbonate, chloride, citrate, fluoride, nitrate, nitrite, oxide, phosphate, and sulfate.

The aqueous solution may comprise suitable weak acids and its conjugate bases capable of provided a pH around 7, such as a pH between 6.5 and 7.5. Useful buffering agents for maintaining a pH in the range of between pH 6.5 and 7.5 may be selected from carbonic acid ($H_2CO_3$), bicarbonate ($HCO_3^-$), citric acid, monopotassium phosphate ($KH_2PO_4$), boric acid ($H_3BO_3$), diethyl barbituric acid, MOPS (3-(N-morpholino)propanesulfonic acid) and disodium phosphate ($Na_2HPO_4$). Disodium phosphate and citric acid may be combined to form a buffer stabilizing the pH around 7. The combination of monopotassium phosphate ($KH_2PO_4$), boric acid ($H_3BO_3$), diethyl barbituric acid may also provide a buffer solution providing a pH of around 7. To accelerate exchange, the transformation is preferably carried out at a temperature above 20° C., in particular above 30° C. or even at or above 50° C.

The proto-microelectrode of the invention and a method for its manufacture will now be explained in more detail by reference to a preferred embodiment illustrated in a drawing comprising a number of figures. For the sake of visual clarity different elements of the pre-stage and proto-microelectrodes illustrated in the figures are not to scale.

SHORT DESCRIPTION OF THE FIGURES

Except for FIGS. 2*a* and 18, all figures are longitudinal sections of proto-microelectrodes or their pre-stages and of containers used in their production.

FIGS. 1 through 16 illustrate the manufacture of a first embodiment of the proto-microelectrode of the invention; and the proto-microelectrode FIGS. 1, 1*a* illustrate a cylindrical (central axis A-A), partially insulated microelectrode body for use in the invention, in a sectional view (FIG. 1), and an enlarged partial sectional view of its terminal proximal portion (FIG. 1*a*), the insulation extending proximally of the microelectrode body to cover and insulated a flexible electrically conducting lead connecting the microelectrode body with an apparatus for electrode control (not shown);

FIG. 2 shows, in a longitudinal section (axis C-C), a first container consisting of two halves kept together by an annular retainer and comprising a cylindrical channel closed its bottom end;

FIG. 2*a* is a top view in a distal direction of the electrode body inserted into the first container;

FIG. 17 shows a cylindrical (central axis A'-A') microelectrode body lacking electrical insulation for use in the invention to the distal terminal portion of which a flexible electrically conducting lead is connected to provide for electrical connection of the microelectrode body with an apparatus for electrode control (not shown);

FIGS. 18, 19 show the microelectrode body of FIG. 17 inserted into the first container of FIG. 2 in a manner to make their axes A'-A' and C-C coincide;

FIG. 20 shows the void between the electrode body and the inner wall of the first container filled with a concentrated aqueous solution of glucose;

FIG. 21 shows the aqueous solution of glucose in the void of FIG. 20 in a frozen state;

FIG. 22 shows a first pre-stage of the electrode of the invention formed by removing the electrode body with the frozen solution adhering to its lateral and distal faces from the first container;

FIG. 23 shows a second pre-stage of the electrode of the invention of which the electrode body is covered with a porous layer of dry glucose formed by freeze-drying of the first pre-stage's frozen glucose solution;

Figures 6, 7, 8, 9:
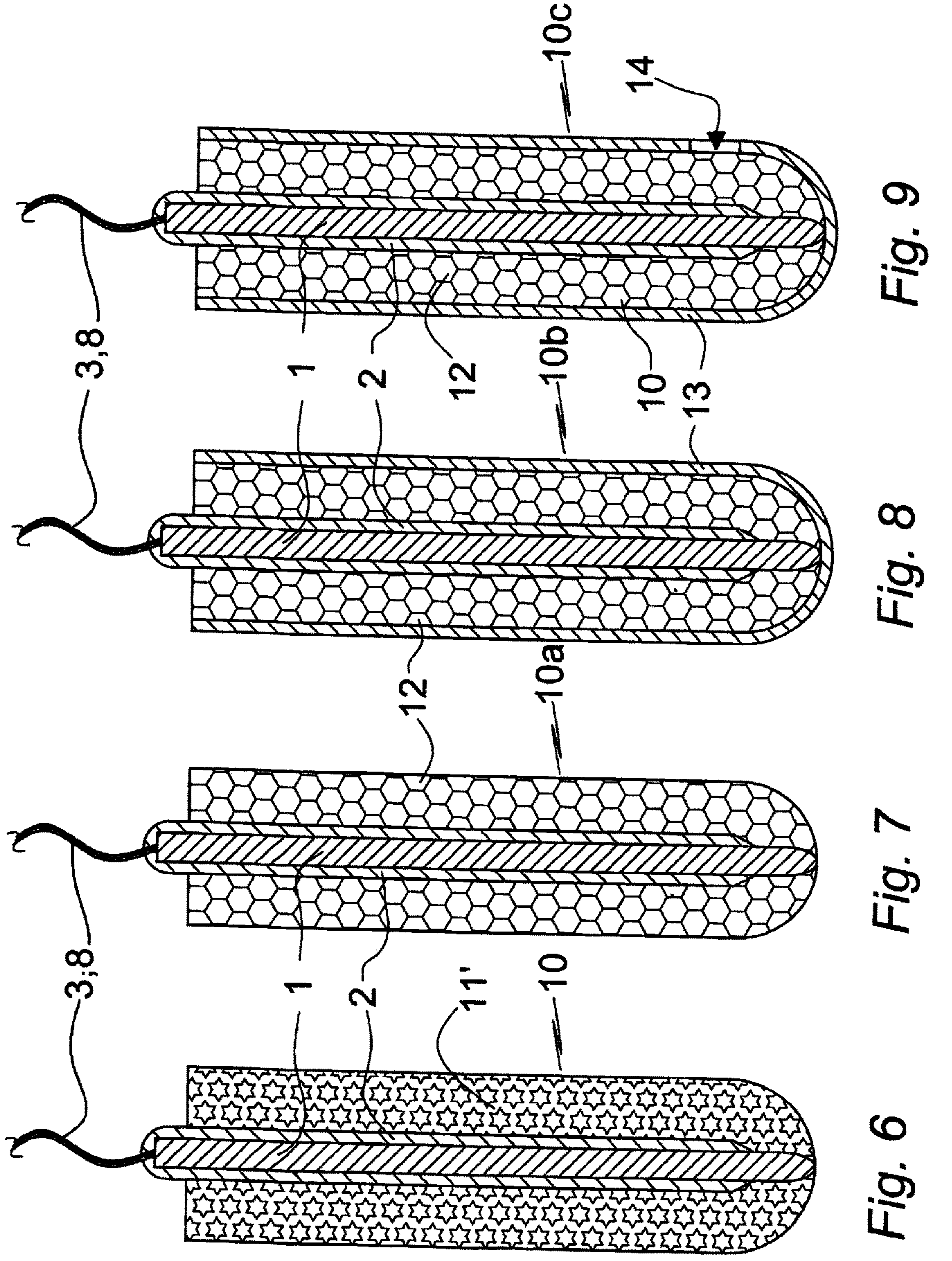
FIG. 6 shows a first pre-stage of the electrode of the invention formed by removing the electrode body with the frozen solution adhering to its lateral and distal faces from the first container.
FIG. 7 shows a second pre-stage of the electrode of the invention of which the electrode body is covered with a porous layer of dry glucose formed by freeze-drying of the first pre-stage's frozen glucose solution.
FIG. 8 shows a third pre-stage of the electrode of the invention comprising a coat of water-insoluble flexible polymer disposed on the external face of the layer of porous dry glucose, the polymer layer having been formed by gaseous deposition of polymer precursors.
FIG. 9 shows the third pre-stage of FIG. 8 provided with a lateral opening or window in the coat of water-insoluble flexible polymer.
Figure 25:
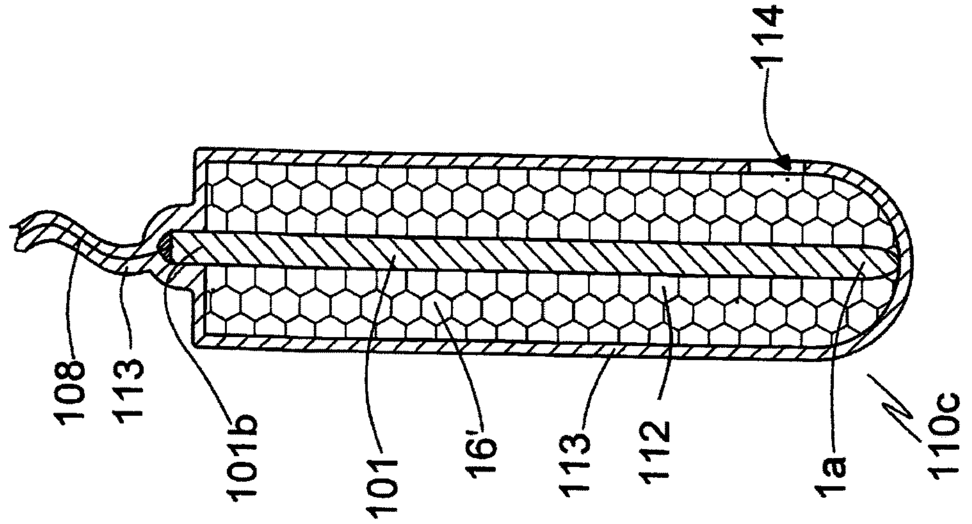
Figure 24:
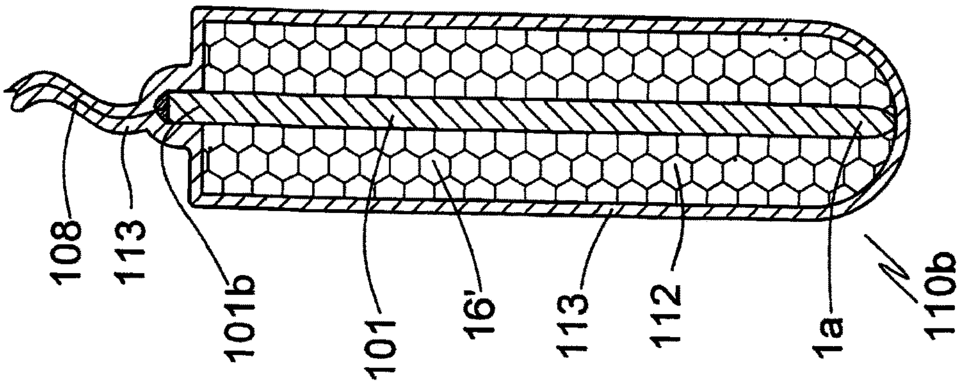
Figures 26, 27, 28, 29:
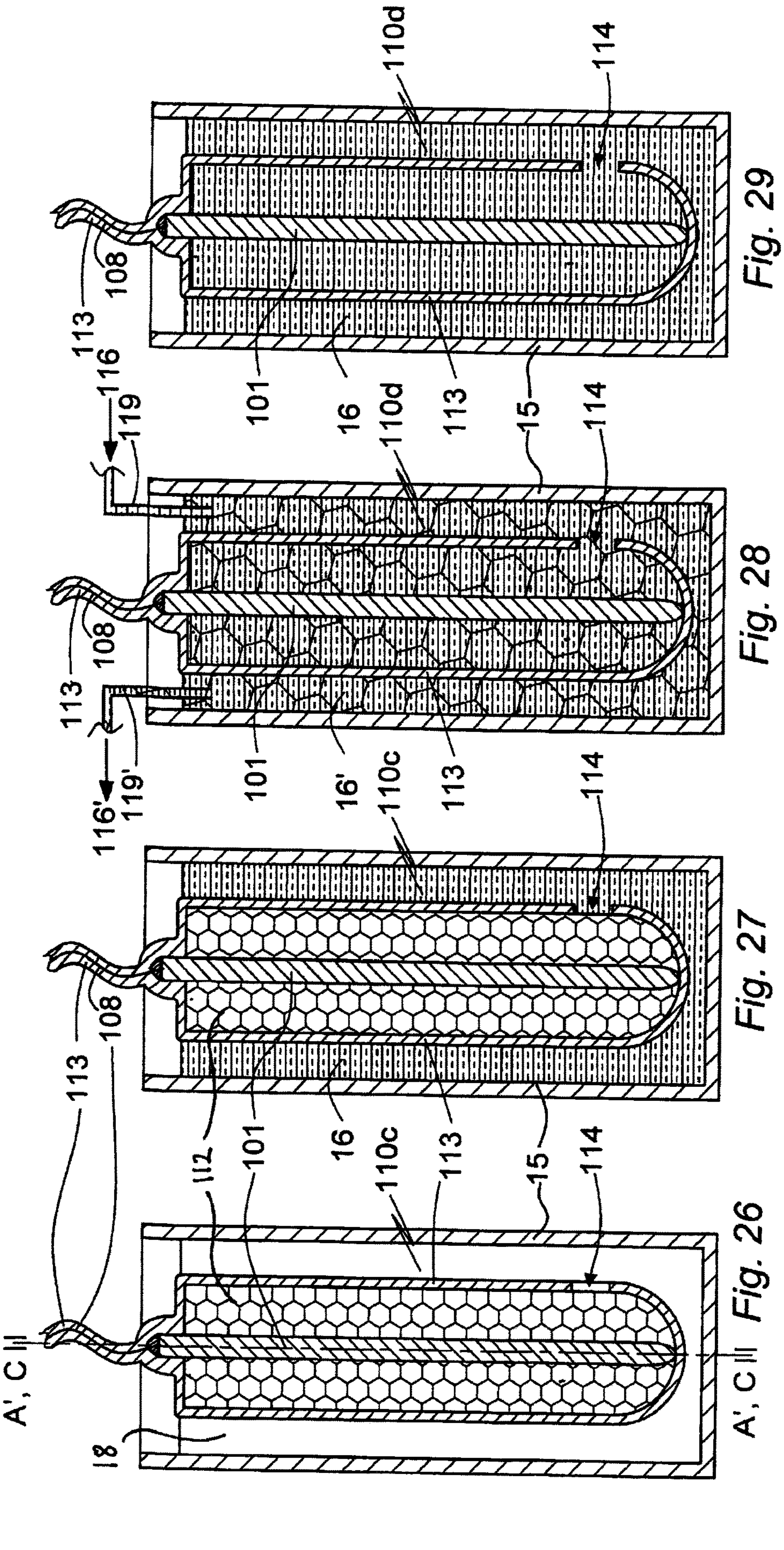
Figure 32:
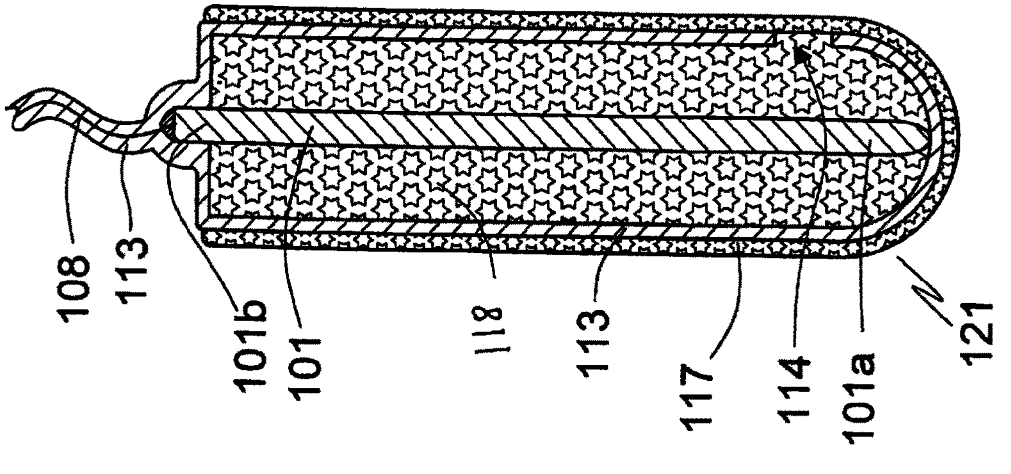
Figure 31:
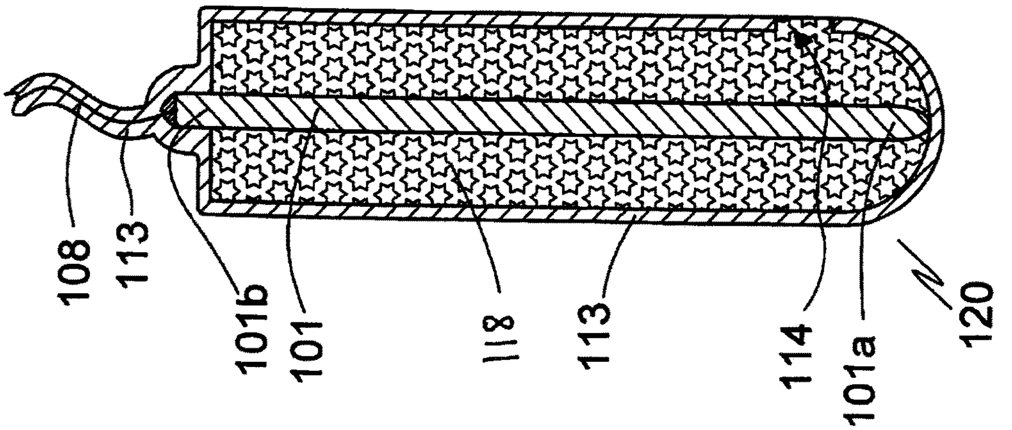
Figure 30:
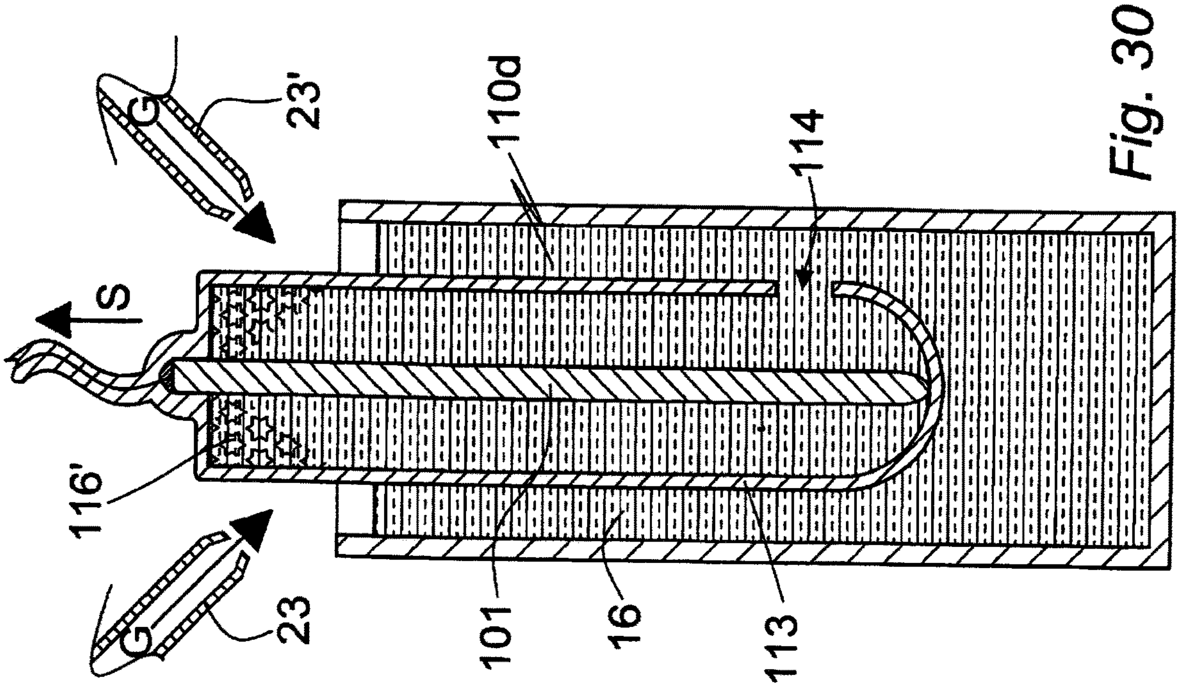

FIG. 24 shows a third pre-stage of the electrode of the invention comprising a coat of water-insoluble flexible polymer disposed on the external face of the layer of porous dry glucose, the polymer layer having been formed by gaseous deposition of polymer precursors. The coat water-insoluble flexible polymer extends proximally of the electrode body to cover and thereby isolate the flexible electrically conducting lead;

FIG. 25 shows the third pre-stage of FIG. 8 provided with a lateral opening or window in the coat of water-insoluble flexible polymer;

FIG. 26 shows the modified third pre-stage of FIG. 25 inserted into the cylindrical void of the second container in a manner making their axes A', D coincide;

FIG. 27 shows the modified third pre-stage of FIG. 26 immediately upon filling the void between the third pre-stage and the inner wall of the second container with water optionally comprising small amounts of soluble additives such as pharmaceuticals and vitamins;

FIG. 28 illustrates the action of water optionally comprising small amounts of soluble material on the third pre-stage in the second container upon storing for a time causing dissolution of the porous glucose layer;

FIG. 29 illustrates the substitution of the aqueous solution of glucose inside of the layer of flexible, water insoluble polymer material of the third pre-stage by diffusion/convection of water optionally containing small amounts of soluble material added to and withdrawn from the container continuously or discontinuously;

FIG. 30 shows the third pre-stage of the proto-microelectrode being withdrawn from the second container while cooling by a flow of cold gas directed at the portion of the third pre-stage emanating from the second container;

FIG. 31 shows the proto-microelectrode of the invention formed from the third pre-stage of during its withdrawal from the second container;

FIG. 32 shows a first variety of the proto-microelectrode of the invention with its coat of polymer material covered by a thin layer of ice.

DESCRIPTION OF PREFERRED EMBODIMENTS

Figures 1, 1A, 2, 2A, 3, 4, 5:
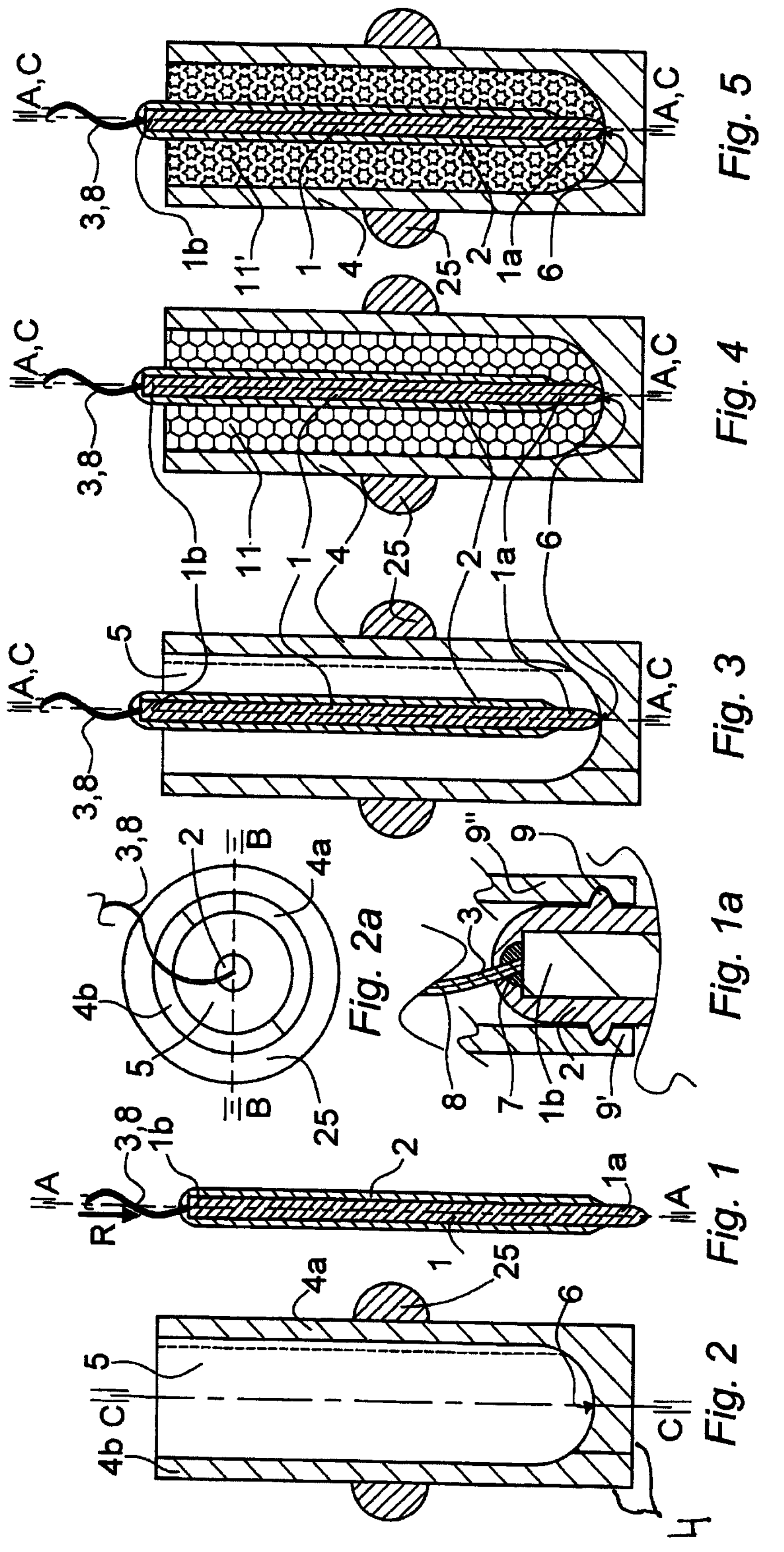
FIG. 3 shows the insulated microelectrode body of FIG. 1 inserted into the first container of FIG. 2 in a manner to make their axes A-A and C-C coincide.
FIG. 4 shows the void between the electrode body and the inner wall of the first container filled with a concentrated aqueous solution of glucose.
FIG. 5 shows the aqueous solution of glucose in the void of FIG. 4 in a frozen state.

Example 1. Manufacture of a First Embodiment of the Proto-Microelectrode of the Invention An oblong cylindrical microelectrode body 1 of an electrically conducting material such as, for instance, copper, silver, gold or platinum, having a central axis A-A is covered by a coat 2 of an insulating material, in particular of a polymer material, extending from its rear (proximal) terminal portion 1*b* towards its front (distal) end in a manner so as to leave a distal terminal portion 1*a* of the electrode body 1 uncovered (FIG. 1*a*). Attached to the proximal end of the proximal terminal portion 1*b* by solder 7 is a flexible metallic wire 8 covered with an insulating coat 3 of lacquer or polymer material (FIG. 1*b*). At its other end, the wire 8 is connected to an apparatus (not shown) for electrical control of and/or receipt of electrical signals from the electrode body 1. In a variety of the microelectrode of the invention illustrated in FIG. 17 and its various pre-stages (not shown), the coat 2 of insulating material can extend proximally of the electrode body 1 for insulation of the flexible metallic wire 8, thereby making the separate insulation layer 3 redundant.

The electrically insulated rear or proximal terminal portion 1*b* of the partially insulated electrode body 1, 2 is shown in FIG. 1*a* enlarged and in greater detail. It comprises, at a short distance from its proximal end, an annular bulge 9 allowing arms 9', 9" of a pincer-like gripping device to hold it for manipulation. For the sake of reducing visual complexity in the drawing, the annular bulge 9 comprised by all microelectrode bodies 1 of FIGS. 3 through 13 is only shown in FIG. 1*a*.

A first container 4 comprises a cylindrical channel 5 having an upper open end and a bottom end 6 of rounded form, such as of hemi-circular or hemi-elliptical form, is shown in FIG. 2 in an axial section B-B (FIG. 2*a*). The first container 4 is of a low-friction material such as polypropylene, polyfluorinated polyalkene or silicone, or has the face of its channel 5 covered with a layer of such material. It comprises two symmetrical halves 4*a*, 4*b* releaseably joined by an annular retainer 25 at their mutually abutting flat faces extending in the longitudinal direction of the container.

The partially insulated microelectrode body 1, 2 is inserted into the cylindrical channel 5 with its distal end 1*a* foremost (direction R) in a centered manner to make its axis A-A coincide with the channel axis C-C. The insertion is to a depth in the vicinity of the hemi-circular bottom or until the front end of the distal portion 1*a* is contacting the bottom 6, as shown in FIG. 3. Alternatively, its distal end can be disposed at a short distance from the bottom 6 (not shown).

Upon insertion of the partially insulated microelectrode body 1, 2, the remaining void of channel 5 is filled with an aqueous solution 11 comprising 45% by weight of glucose up to about the height of the insulated proximal terminal microelectrode body portion 1*b* (FIG. 4).

Next, the first container 4 with its contents 1, 2, 11 is cooled to a sufficiently low temperature, such as to a temperature of −15° C. or −20° C., thereby transforming it into a frozen state 11' (FIG. 5) to make the contents 1, 2, 11' in combination with the distal terminal portion 1*b* of the electrode body 1 and the insulated 8 electrical lead 3 constitute the in-situ first pre-stage of the microelectrode of the invention. The contents 1, 2, 11' are then withdrawn from the first container 4 by releasing the retainer 25 to isolate the first pre-stage 10 of the microelectrode of the invention (FIG. 6).

While the first pre-stage 10 is kept at a low temperature to prevent the frozen glucose solution 11' from thawing, it is exposed to low pressure, such as a pressure of 0.1 mm Hg or 0.01 mm Hg or lower, for a sufficient period of time to transform its frozen glucose layer 11' to a porous layer 12 of dry glucose. The so produced second pre-stage 10 a of the microelectrode of the invention is shown in FIG. 7.

Alternatively the container 4 with the partially insulated electrode body 1, 2 covered by frozen aqueous carbohydrate solution 11' is placed in an oven and heated to a temperature above room temperature, in particular to a temperature of 50° C. or more, until the aqueous solution has been transformed to a caramelized first carbohydrate layer on the electrode body 1, 2 and the assembly thus to a second pre-stage microelectrode.

Next, the distal and lateral face of the porous glucose layer 12 of the second pre-stage 10 a is covered with a silicone polymer coat 13 by dip coating (FIG. 8). The thickness of the polymer coat 12 of the thus produced third pre-stage 10*b* of the microelectrode of the invention is from about 2 μm to about 5 μm.

In the following step one or more openings or windows 14 are provided in a distal portion of the polymer coat 13 by removing portions of the coat 13 by a micro-diamond knife or by evaporation by laser means to form the fourth pre-stage 10*c* of the microelectrode of the invention (FIG. 9). When using laser means it is advantageous to evaporate the polymer step-by-step to provide an opening with a smooth contour.

Figures 10, 11, 12, 13:
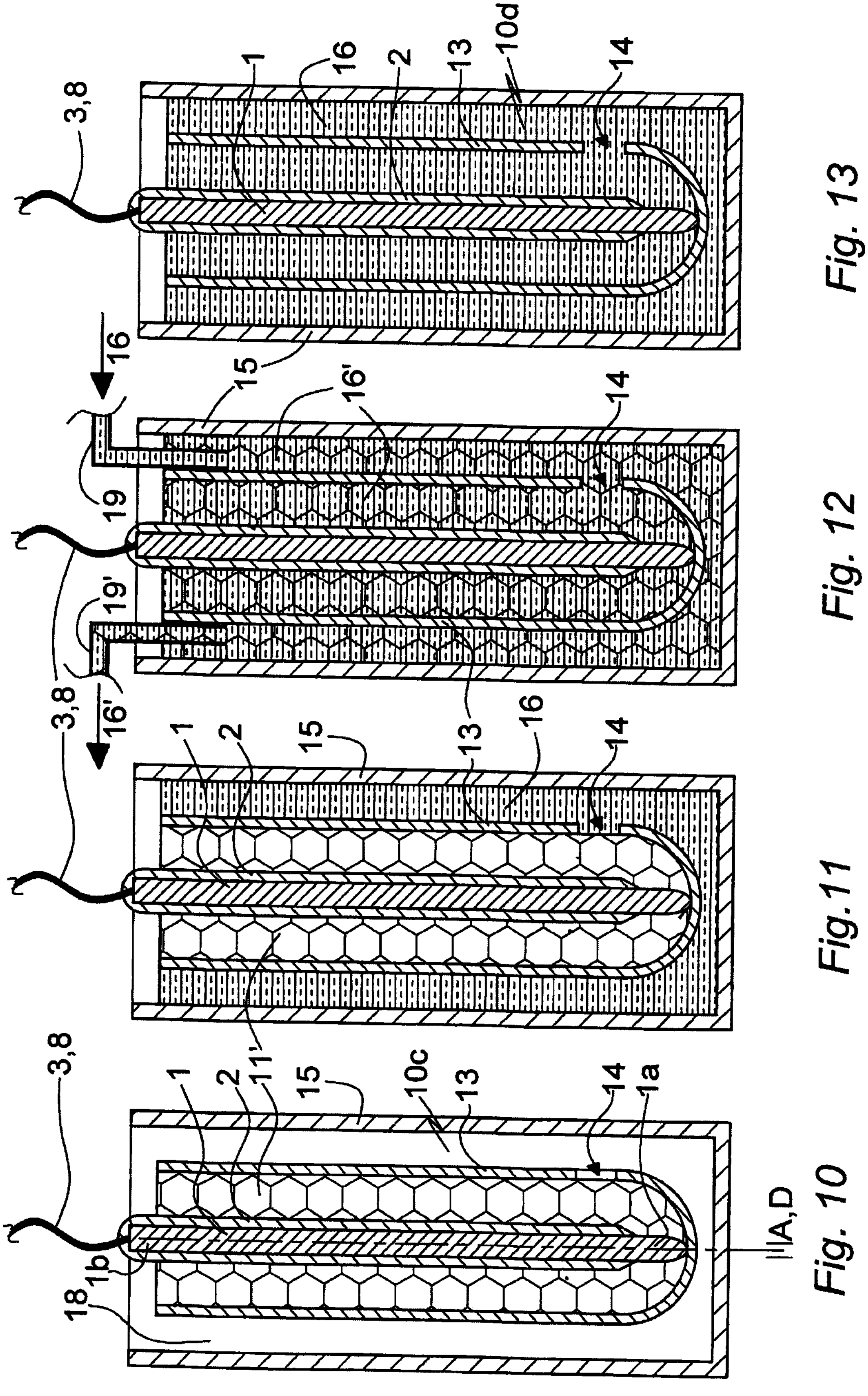
FIG. 10 shows the modified third pre-stage of FIG. 9 inserted into the cylindrical void of a second container in a manner making their axes A, D coincide.
FIG. 11 shows the modified third pre-stage of FIG. 10 immediately upon filling the void between the third pre-stage and the inner wall of the second container with water optionally comprising small amounts of soluble additives such as pharmaceuticals and vitamins.
FIG. 12 illustrates the action of water optionally comprising small amounts of soluble material on the third pre-stage in the second container upon storing for a time causing dissolution of the porous glucose layer.
FIG. 13 illustrates the substitution of the aqueous solution of glucose inside of the layer of flexible, water insoluble polymer material of the third pre-stage by diffusion/convection of water optionally containing small amounts of soluble material added to and withdrawn from the container continuously or discontinuously.

In the first of the final production steps of the proto-microelectrode 20 of the invention (cf. FIG. 15), the fourth pre-stage 10*c* is disposed in the cylindrical void 18 of a second container 15 of, for instance, glass or metal, with its distal end foremost and centered in respect of the container axis D-D (FIG. 10).

Next, the void 18 is filled up to the proximal terminal portion 1*b* of the fourth pre-stage's 10*c* (cf. FIG. 10) microelectrode body 1 with water 16 optionally comprising small amounts of biologically active agent, such as anti-coagulation agent, antibacterial agent, anti-virus agent osmotic pressure controlling agent (FIG. 11); the use of artificially prepared spinal fluid or physiological aqueous solutions for this purpose is recommended.

FIG. 12 illustrates a production stage at which the water or aqueous solution 16 surrounding the fourth pre-stage 10*c* (cf. FIG. 10) has entered through window 14 the space enclosed by the polymer coat 13 containing porous glucose 11', which is dissolved to form a diluted aqueous solution 16' of glucose optionally containing said small amounts of biologically active agent(s).

Further, in particular continuous, provision of water 16 or a diluted aqueous solution 16 optionally containing small amounts of biologically active agent(s) supplied to the second container 2 by one or more feeding tube(s) 19 and draining the liquid contents 16' of the container by one or more draining 19' tubes, results in the aqueous fluid 16' originally present in the second container 2 to be substituted by water 16 optionally containing small amounts of biologically active agent (FIG. 13).

Figure 14:
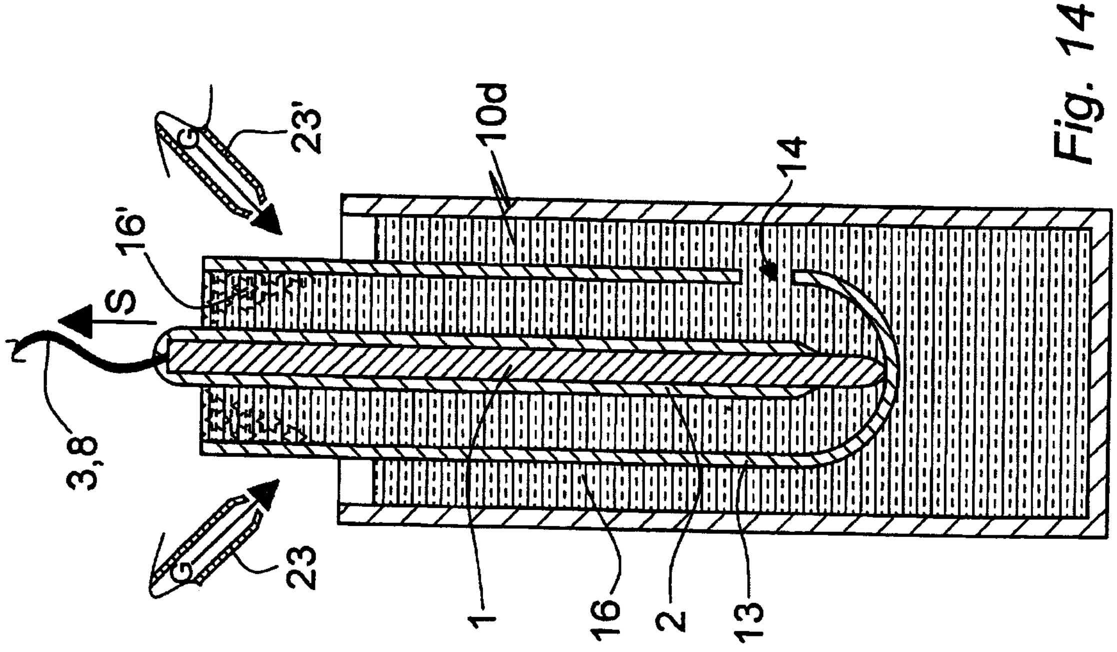
FIG. 14 shows the third pre-stage of the proto-microelectrode being withdrawn from the second container while cooling by a flow of cold gas directed at the portion of the third pre-stage emanating from the second container.

In the final production step the so formed in-situ fifth pre-stage 10*d* of the proto-microelectrode of the invention is slowly withdrawn (in axial direction S) from the second container 2 (FIG. 14) while cooling it with a stream of cold gas G at a temperature of −20° C. or lower, such as with air or nitrogen or carbon dioxide formed from dry ice, fed by tubes 23, 23' with their outlet openings pointing towards pre-stage 10*d* emerging from the second container 2, successively (in parallel with removal) transforming the water or aqueous solution 16 disposed inside of the flexible polymer coat 13 to ice 16'. In this manner pre-stage 10*d* is transformed to the proto-microelectrode of the invention 20 (FIG. 15) of which the entire space between the partially insulated electrode body 1, 2 and the coat 13 of flexible polymer material is filled with ice 16 optionally comprising small amounts of biologically active agent.

Figure 16:
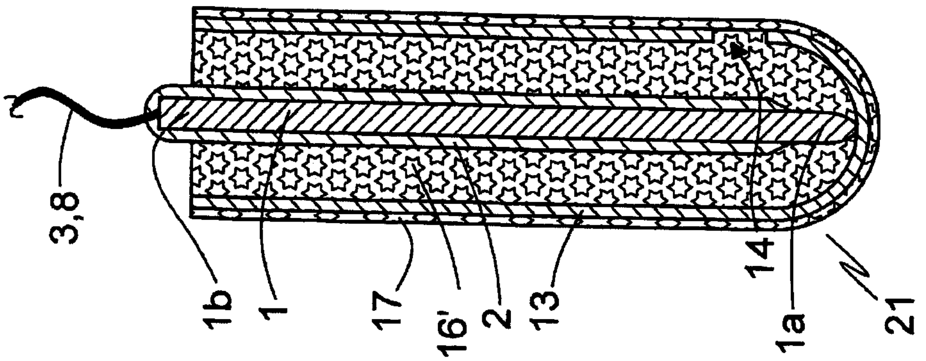
FIG. 16 shows a first variety of the proto-microelectrode of the invention with its coat of polymer material covered by a thin layer of ice.

The first variety 20*a* of the proto-microelectrode 20 of the invention shown in FIG. 16 additionally comprises a second layer 17 of ice optionally comprising biologically active agent(s) on the distal and lateral portions of the electrode 20 covered by the flexible polymer layer 13 and including the window 14.

Figure 15:
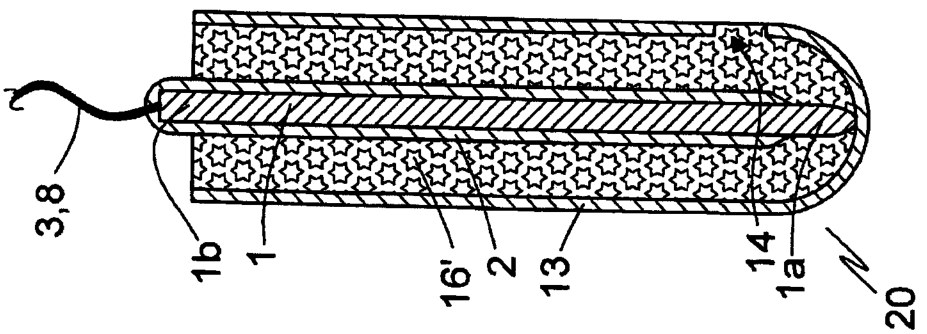
FIG. 15 shows the proto-microelectrode of the invention formed from the third pre-stage of during its withdrawal from the second container.

FIG. 16 shows a second variety 21 of the proto-microelectrode of the invention in which the flexible polymer coat 13' disposed on the first layer of ice 16' optionally comprising small amount(s) of biologically active agent(s) extends distally of the distal terminal portion 1*b* of the electrode body 1 so as to cover the flexible electrical lead 8, which thus does not require separate insulation. In the production of variety 21 the polymer coat 13' (to be later provided with opening(s) or window(s) 14') is applied to the second pre-stage 10*a* instead of the polymer coat 13 (FIG. 7). Since being substantially identical with corresponding production stages resulting in the proto-microelectrode of the invention 20, the corresponding stages of manufacture of the second variety 21 of the proto-microelectrode of the invention intermediate between those shown in FIGS. 5 and 15 are not separately illustrated.

Figures 17, 18, 19, 20, 21:
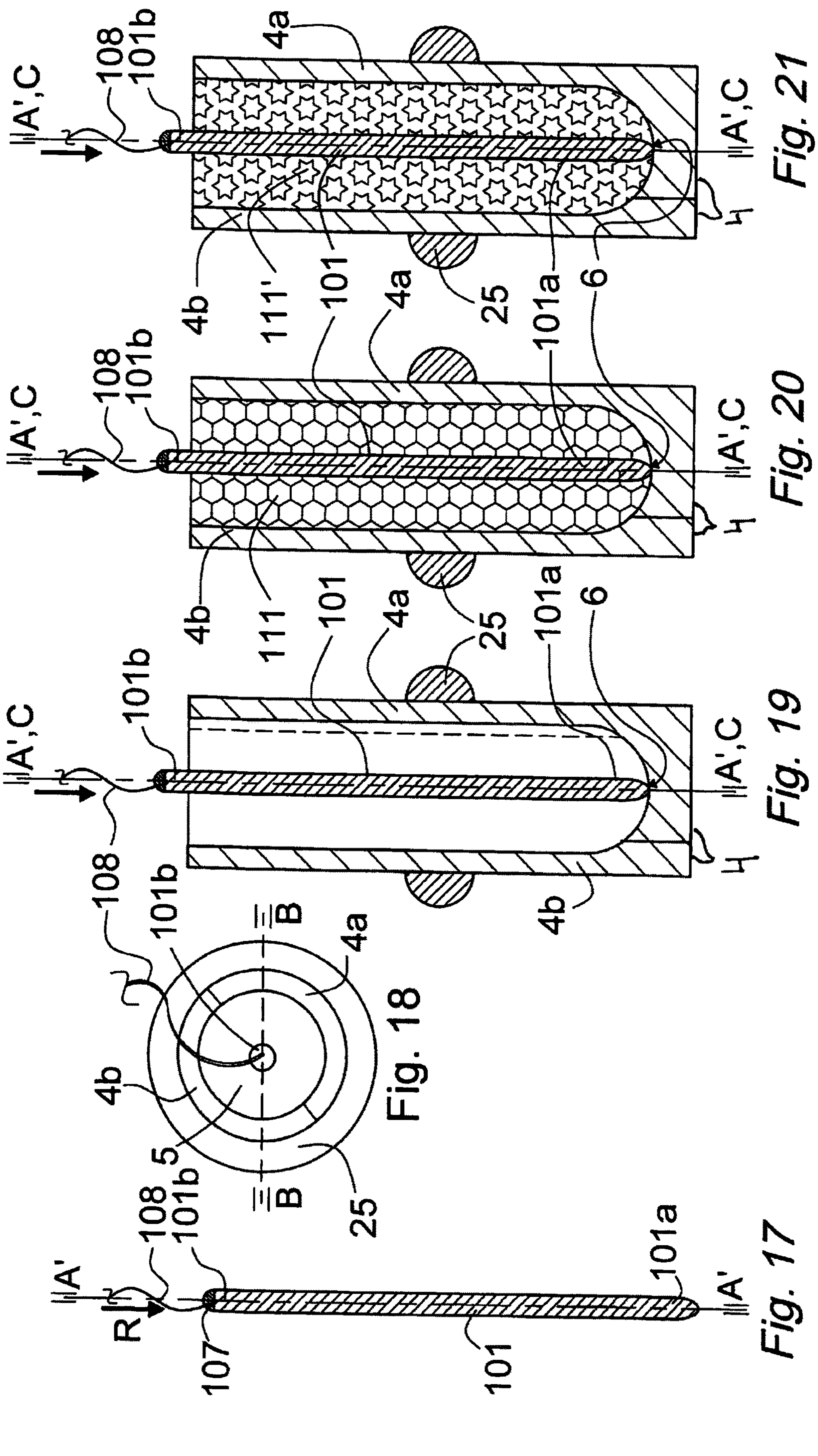
FIGS. 17 through 32 illustrate the manufacture of a second embodiment of the proto-microelectrode of the invention; and the proto-microelectrode.

FIG. 18 shows a second variety 22 of the proto-microelectrode of the invention differing from the first variety 21 by lacking insulation 2 on the electrode body 1 while sharing all other features.

Example 2. Manufacture of a Second Embodiment of the Proto-Microelectrode of the Invention Attached by solder 107 to the proximal terminal portion 101*b* of an oblong cylindrical microelectrode body 101 of an electrically conducting material such as, for instance, copper, silver, gold or platinum, having a central axis A'-A' is a flexible metallic wire 108 (FIG. 17). At its other end, the wire 108 is connected to an apparatus (not shown) for electrical control of and/or receipt of electrical signals from the electrode body 101.

Upon insertion of the microelectrode body 101 into the cylindrical channel 5 of the first container 4*a*, 4*b* of FIG. 19 with its distal end 101*a* foremost and in a centered manner to make its axis A'-A' coincide with the channel axis C-C and to a depth in the vicinity of the hemi-circular bottom or until the front end of the distal portion 101*a* is contacting the bottom 6 (FIGS. 19, 20, 21), the remaining void of the first container 4*a*, 4*b* is filled with an aqueous solution 111 comprising 45% by weight of glucose to about the height of the proximal terminal microelectrode body portion 101*b* (FIG. 20).

Figure 22:
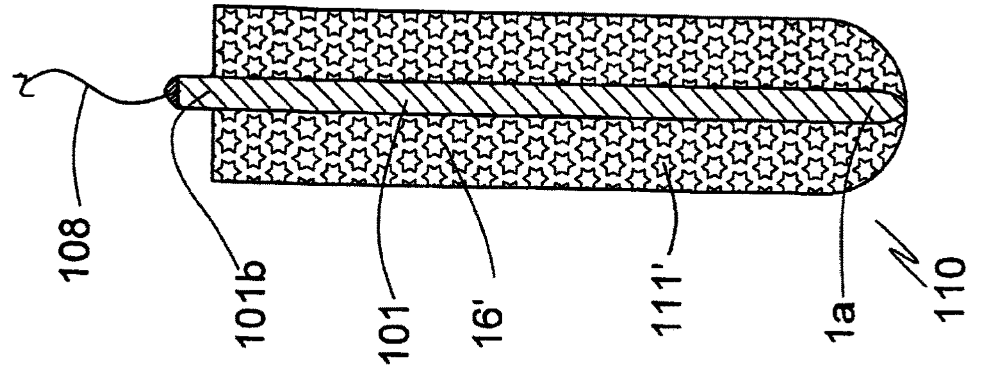

Next, the first container 4 with its contents 101, 111 is cooled to a low temperature, such as to a temperature of −15° C. or −20° C., sufficient for transforming the aqueous glucose solution 111 into a frozen state 111' (FIG. 21), thereby making the contents 101, 111' in combination with the proximal terminal portion 101*b* of the electrode body 101 not covered by frozen glucose solution 111' and the electrical lead 108 constitute a direct precursor of the first pre-stage of the microelectrode of the invention (FIG. 21). The contents 101, 111' are then removed from the first container 4 by releasing the retainer 25 to provide the first pre-stage 110 of the microelectrode of the invention (FIG. 22).

Figure 23:
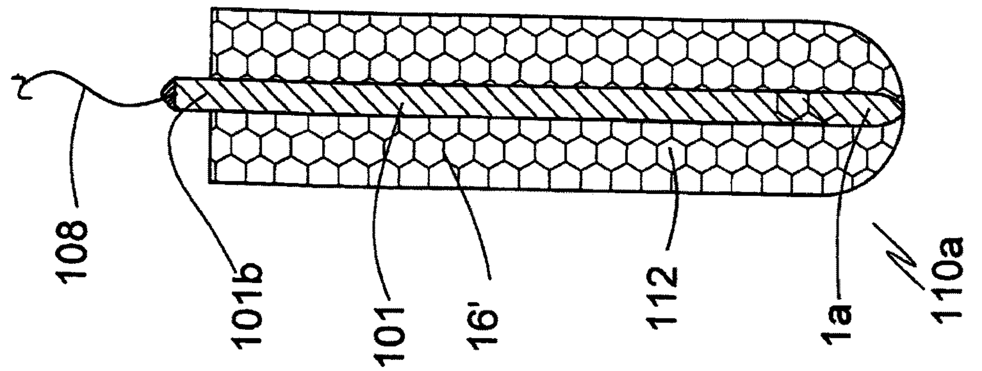

While the first pre-stage 110 is kept at a low temperature to prevent the frozen glucose solution 111' from thawing, it is exposed to a low pressure, such as a pressure of 0.1 mm Hg or 0.01 mm Hg or lower, for a sufficient period of time to transform its frozen glucose layer 111' to a porous layer 112 of dry glucose. The so produced second pre-stage 110*a* of the microelectrode of the invention is shown in FIG. 23. Alternatively, the container 4 with the electrode body 101 covered by frozen aqueous carbohydrate solution 111' is placed in an oven and heated to a temperature above room temperature, in particular to a temperature of 50° C. or more, until the aqueous solution has been transformed to a caramelized first carbohydrate layer on the electrode body 1 and the assembly thus to a second pre-stage microelectrode.

Next, the distal and lateral face of the porous glucose layer 112 of the second pre-stage 110*a* is covered up to its proximal end with a polymer coat 113 of Parylene C by evaporation and deposition of Parylene C precursors at low pressure (FIG. 24). The thickness of the polymer coat 113 of the thus produced third pre-stage 100*b* of the microelectrode of the invention is from about 2 μm to about 5 μm. The Parylene C coat then further extends proximally to cover, thereby electrically isolating the connecting wire or lead 108.

In the following step one or more openings or windows 114 are provided in a distal portion of the polymer coat 113 by removing portions of the coat 113 by a micro-diamond knife or by evaporation by laser means to form the fourth pre-stage 110*c* of the microelectrode of the invention (FIG. 25).

In the first of the final production steps of the second embodiment of the proto-microelectrode 120 of the invention, the fourth pre-stage 110*c* is disposed in the cylindrical void 18 of the second container 15 of FIG. 26.

Next, the void 18 with the fourth pre-stage electrode 110*c* is filled up to the proximal terminal portion 101*b* (FIG. 27) with water 16.

By successively dissolving the porous glucose layer 112 (by water or aqueous solution comprising biologically active agents) added water 16 or aqueous solution 16 containing small amounts of biologically active agent(s) then enters through window 114 the space enclosed by the polymer coat 113 to form an aqueous solution 16' of glucose optionally containing small amounts of biologically active agent, such as anti-coagulation agent, antibacterial agent, anti-virus agent osmotic pressure controlling agent (FIG. 28). Further, in particular continuous, supply of water 116 optionally containing small amounts of biologically active agent(s) to the second container 15 by one or more feeding tube(s) 119 and draining the liquid contents 116' of the container by one or more draining 119' tubes results in the aqueous fluid 16' originally present in the second container 15 to be substituted by water 16 optionally containing small amounts of biologically active agent (FIG. 29).

In the final production step the so formed in-situ fifth pre-stage 110*d* of the second embodiment of the proto-microelectrode of the invention is slowly withdrawn (in axial direction S) from the second container 15 (FIG. 30) while cooling it with a stream of cold gas G at a temperature of −20° C. or lower, such as with air or nitrogen or carbon dioxide formed from dry ice, fed by tubes 23, 23' with their outlet openings pointing towards pre-stage 110*d* emerging from the second container 15, successively (in parallel with removal) transforming the water or aqueous solution 16 disposed inside of the flexible polymer coat 113 to a layer of ice 118. In this manner pre-stage 110*d* is transformed to the second embodiment of the proto-microelectrode of the invention 120 (FIG. 31) of which the entire space between the electrode body 101 and the coat 113 of flexible polymer material is filled with ice 118, optionally comprising small amounts of biologically active agent.

A first variety 121 of the proto-microelectrode 120 of the invention is shown in FIG. 32. It comprises additionally a second layer 117 of ice optionally comprising biologically active agent(s) on the distal and lateral portions of the flexible polymer layer 113 and on the portion of the ice 116' layer at window 114 not covered by layer 113.

The invention claimed is:

1. Proto-microelectrode capable of forming, upon insertion into soft tissue, a microelectrode, the proto-microelectrode comprising:
- an oblong electrode body of electrically conducting material having a front end and a rear end, the electrode body comprising metal or metal alloy or an electrically conducting form of carbon or an electrically conducting polymer or a combination thereof;
- an optional first coat of electrically non-conducting material on the electrode body extending along it from its rear end towards its front end, the electrode body comprising one or more sections not covered by the first coat;
- a second coat of water-insoluble flexible polymer material disposed at a distance from and enclosing the electrode body and, if present, the first coat or a portion thereof, the second coat comprising one or more through openings or windows;
- a first layer of ice comprising pharmacologically active agent disposed between the electrode body and the second coat.

2. The proto-microelectrode of claim 1, wherein the electrode body is resiliently flexible.

3. The proto-microelectrode of claim 1, wherein the first layer of ice has a melting point of from −5° C. to 0° C.

4. The proto-microelectrode of claim 1, wherein one or more of said one or more through openings are disposed in a distal portion or distal portions of the second coat.

5. The proto-microelectrode of claim 1, wherein one or more of said one or more through openings are disposed in a portion of the second coat extending from half of its length to a distal end of the electrode body.

6. The proto-microelectrode of claim 1, wherein one or more of said one or more through openings are disposed in a portion of the second coat extending from half of its length to a proximal end.

7. The proto-microelectrode of claim 1, wherein the second coat has a wall thickness that is smaller than the diameter of the electrode body or the diameter of the combination of electrode body and first coat.

8. The proto-microelectrode of claim 7, wherein the wall thickness of the second coat is up to 20 μm.

9. The proto-microelectrode of claim 1, wherein the diameter of the electrode body is from 1 μm to 100 μm.

10. The proto-microelectrode of claim 1, wherein a portion of the second coat has the form of a bellows tube.

11. The proto-microelectrode of claim 1, comprising an electrical lead attached to a proximal portion of the electrode body, wherein the second coat extends to and encloses a distal portion of the lead.

12. The proto-microelectrode of claim 1, comprising a second layer of ice optionally comprising pharmacologically active agent disposed on the second coat.

13. The proto-microelectrode of claim 1, wherein the ice comprises any combination of ammonium, calcium, iron, magnesium, potassium, quaternary ammonium, sodium, copper, acetate, carbonate, chloride, citrate, fluoride, nitrate, nitrite, oxide, phosphate, and sulfate.

14. The proto-microelectrode of claim 1, wherein the ice comprises a buffer capable of regulating the pH of the aqueous solution prior to freezing between 6.5 up to 7.5.

15. A method of generating a micro-electrode disposed in soft tissue comprising inserting the proto-microelectrode of claim 1 into the tissue, wherein the proto-microelectrode has a temperature at the start of insertion of below 0° C.

16. A method comprising monitoring electrochemical signals using the proto-microelectrode of claim 1.

17. Method of manufacture of a proto-microelectrode for insertion into soft tissue, comprising:

providing a first pre-stage microelectrode comprising: an oblong electrode body of electrically conducting material having a front end and a rear end; optionally comprising a first coat of electrically non-conducting material on the electrode body extending along it from its rear end towards its front end, the electrode body comprising one or more sections not covered by the first coat; a second coat of water insoluble flexible polymer material disposed at a distance from and enclosing the electrode body or a portion thereof, the second coat comprising one or more through openings; a layer of porous carbohydrate material disposed between the electrode body and the second coat;

providing a second pre-stage microelectrode by substituting the layer of porous carbohydrate material by water optionally comprising pharmacologically active agent;

cooling the thus transformed second pre-stage microelectrode to a temperature capable of transforming the layer of water optionally comprising pharmacologically active agent to a first layer of ice for a time sufficient for complete transformation.

18. The method of claim 17, comprising:

optionally providing the second coat with a layer of gelatin;

providing the second coat or, if present, the layer of gelatin on the second coat with a second layer of ice optionally comprising pharmacologically active agent.

19. The method of claim 17, wherein the first pre-stage microelectrode comprises a flexible electrical lead attached to the proximal end of the electrode body and wherein the second coat encloses a distal terminal portion of the flexible electrical lead.

20. The method of claim 17, wherein the layer of porous carbohydrate material on the electrode body is formed by providing an aqueous solution comprising water and more than 20% by weight of glucose and/or other mono- or disaccharide of high solubility in water or a combination thereof; providing a form comprising a channel of cylindrical form or other rotationally symmetric form closed at one of its ends; disposing the electrode body with its distal end foremost in the channel; filling the channel up to a desired proximal level of the electrode body with said aqueous solution; cooling the form to a freezing temperature of the aqueous solution; separating the electrode body with adhering frozen aqueous solution from the form and disposing it either, while keeping it frozen, in an low-pressure environment for a time sufficient to transform the frozen aqueous solution to said layer of porous carbohydrate, wherein a pressure in the low-pressure environment is below 1000 Pa, or placing a container with its contents in an oven, heating the container with its contents to a temperature above room temperature until the aqueous solution has been transformed to a caramelized first carbohydrate layer on the electrode body and an assembly to a second pre-stage microelectrode.

21. The method of claim 20, wherein the form is separable in a plane in which the cylinder axis or the axis of a channel of other rotationally symmetric form is disposed.

22. Proto-microelectrode array comprising two or more proto-microelectrodes according to claim 1 joined at proximal portions thereof by an array base.

23. Proto-microelectrode bundle comprising two or more proto-microelectrodes according to claim 1 and a bundling element enclosing proximal portions of the two or more proto-microelectrodes.

* * * * *